US010338084B2

(12) United States Patent
Egan et al.

(10) Patent No.: US 10,338,084 B2
(45) Date of Patent: Jul. 2, 2019

(54) PROCESSING REAGENT AND USE THEREOF IN ASSAYS FOR DETECTION OF ANALYTES ASSOCIATED WITH A BINDING PROTEIN

(71) Applicant: Quidel Corporation, San Diego, CA (US)

(72) Inventors: Richard L. Egan, Oceanside, CA (US); Judson McFarland, San Diego, CA (US); Mark Renshaw, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 15 days.

(21) Appl. No.: 15/482,332

(22) Filed: Apr. 7, 2017

(65) Prior Publication Data

US 2017/0292964 A1    Oct. 12, 2017

Related U.S. Application Data

(60) Provisional application No. 62/319,690, filed on Apr. 7, 2016.

(51) Int. Cl.
*G01N 33/53* (2006.01)
*G01N 33/82* (2006.01)

(52) U.S. Cl.
CPC .................................. *G01N 33/82* (2013.01)

(58) Field of Classification Search
CPC ............................ G01N 33/53; G01N 33/82
See application file for complete search history.

(56) References Cited

U.S. PATENT DOCUMENTS

| | | | |
|---|---|---|---|
| 5,821,020 A | 10/1998 | Hollis | |
| 7,964,363 B2 | 6/2011 | Armbruster et al. | |
| 8,594,948 B2 | 11/2013 | McGlennen et al. | |
| 2013/0059825 A1 | 3/2013 | Sahakian et al. | |

FOREIGN PATENT DOCUMENTS

EP            0753743    *  1/1997    ............. G01N 33/82

OTHER PUBLICATIONS

Abraham et al , Journal of Immunological Methods,1991; vol. 144, Issue 1, pp. 77-86, Abstract.*
AW and YAP, "Vitamin D Measurements—Facts and Fancies", Laboratory Insights, Proceedings of Singapore Healthcare, vol. 22, No. 3, pp. 227-234 (2013).
Binkley et al., "Assay variation confounds the diagnosis of hypovitaminosis D: a call for standardization", J. Clin. Endocrinol. Metab., vol. 89, No. 7, pp. 3152-3157 (2004).
Danan et al., "Presence of 25-hydroxyvitamin D3 and 1,25-dihydroxyvitamin D3 24-hydroxylase in vitamin D target cells of rat yolk sac", J. Biol. Chem., vol. 257, No. 18, pp. 10715-10721 (1982).
Diamandis, "Detection techniques for immunoassay and DNA probing applications", Clin. Biochem., vol. 23, No. 5, pp. 437-443 (1990).
He et al., "Measurement of circulating 25-hydroxy vitamin d usingthree commercial enzyme-linked immunosorbent assay kits with comparison to liquid chromatography: Tandem mass spectrometry method", ISRN Nutrition, vol. 2013, ID 723139, 6 pages (2013).
Hollis, "Measuring 25-hydroxyvitamin D in a clinical environment: challenges and needs", Am. J. Clin. Nutr., vol. 88, No. 2, pp. 507s-510s (2008).
Kaushik et al., "Studies on manganese (II) catalyzed oxidation of n-methylaniline by periodate ion", Int. J. Chem. Sci., vol. 8, No. 3, pp. 1379-1388 (2010).
Koivula et al., "Four automated 25-OH total vitamin D immunoassays and commercial liquid chromatography tandem-mass spectrometry in Finnish population", Clin. Lab., vol. 59, No. 3-4, pp. 397-405, Original Article DOI: 10.7754/Clin.Lab.2012.120527 (2013).
Koivunen and Krogsrud, "Principles of immunochemical techniques used in clinical laboratories", Labmedicine, vol. 37, No. 8, pp. 490-497 (2006).
Quidel, "25-OH Vitamin D", Technical Data Sheet, MicroVueBone 25-OH Vitamin D EIA—Cat. #8046 (2014).
Ong et al., "Current 25-hydroxyvitamin D assays: do they pass the test?", Clin. Chim. Acta., vol. 413, No. 13-14, pp. 1127-1134 (2012).
Periodate, from Wikipedia, the free encyclopedia, Online article accessed from: http://en.wikipedia.org/wiki/Periodate, 6 pgs., Accessed on Jul. 7, 2014.
Periodic Acid, from Wikipedia, the free encyclopedia, Online article accessed from: http://en.wikipedia.org/wiki/Periodic_Acid, 4 pgs., Accessed on Jun. 3, 2014.
Wallace et al., "Measurement of 25-hydroxyvitamin D in the clinical laboratory: current procedures, performance characteristics and limitations", Steroids, vol. 75, No. 7, pp. 477-488 *Article in Press* DOI: 10.1016/j.steroids.2010.02.012 (2010).

(Continued)

*Primary Examiner* — Julie Wu
*Assistant Examiner* — Carmencita M Belei
(74) *Attorney, Agent, or Firm* — McDermott Will & Emery LLP; Judy M. Mohr

(57) ABSTRACT

Methods for preparing a sample for detection of an analyte of interest that is bound in vivo to a protein are provided. The method comprises providing a processing reagent comprising metaperiodate and contacting a sample suspected of comprising an analyte of interest associated with a protein with the processing reagent to form a mixture. The analyte of interest, if present in the sample (or mixture), is separated from its associated protein for detection of the analyte of interest. In one embodiment, the method is applied to samples for the detection of levels of vitamin D circulating in the blood. Samples are processed using the reagent disclosed herein to separate the analyte of interest, vitamin D or a metabolite thereof, from the vitamin D binding protein and/or albumin, for detection of the analyte separated from its binding protein(s).

9 Claims, 6 Drawing Sheets

(56) References Cited

OTHER PUBLICATIONS

Wootton, "Improving the measurement of 25-hydroxyvitamin D", Clin. Biochem, Rev., vol. 26, No. 1, pp. 33-36 (2005).
Zerwekh, "Blood biomarkers of vitamin D status", Am. J. Clin. Nutr., vol. 84, No. 4, pp. 1087s-1091s (2008).

* cited by examiner

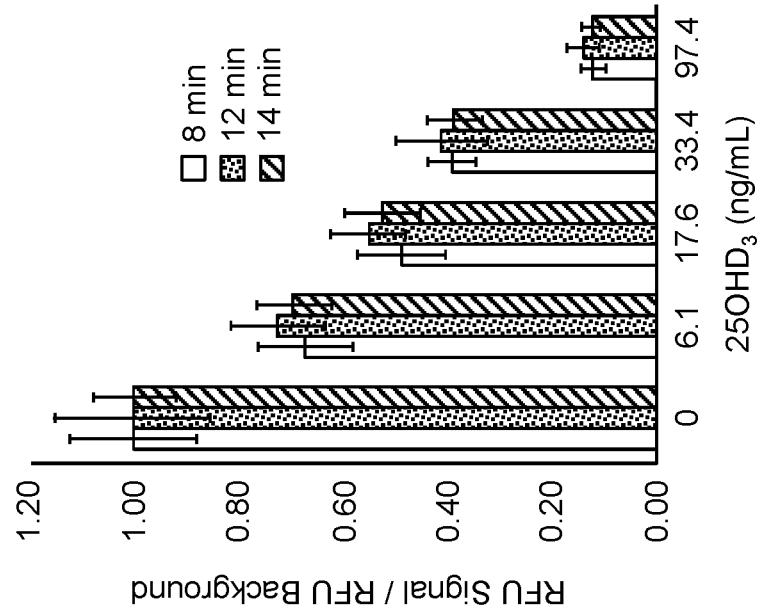
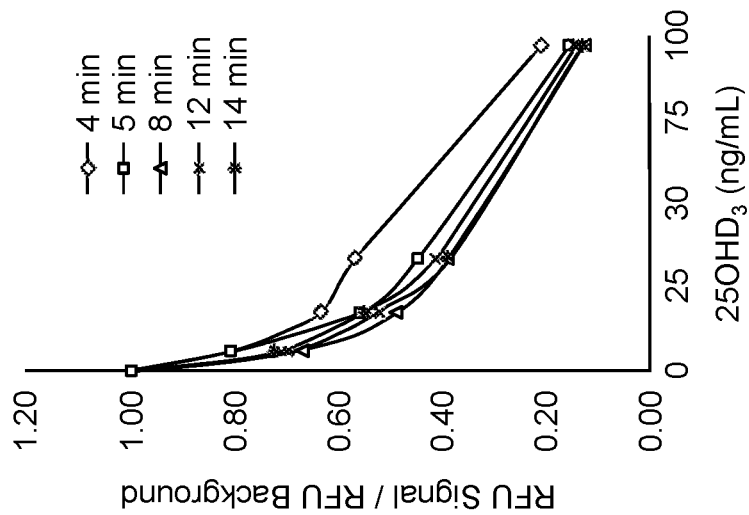
FIG. 2A
FIG. 2B ical field

PROCESSING REAGENT AND USE THEREOF IN ASSAYS FOR DETECTION OF ANALYTES ASSOCIATED WITH A BINDING PROTEIN

CROSS-REFERENCE TO RELATED APPLICATIONS

This application claims the benefit of U.S. Provisional Application No. 62/319,690, filed Apr. 7, 2016, incorporated by reference herein.

TECHNICAL FIELD

The present disclosure is directed to a processing reagent, to methods of its use and to kits comprising the processing reagent, for detecting an analyte of interest that in a sample is associated with a binding protein. The reagent composition is used, in one embodiment, for detecting vitamin D or a metabolite of vitamin D in a blood sample.

BACKGROUND

Detection of analytes in biological samples is a common approach in the diagnostics and treatment area of medicine. In some cases, analytes requiring detection are bound to proteins in vivo, and samples submitted for detection of an analyte are difficult to process and accurately detect due to the interference of a protein bound to the analyte.

One such analyte is vitamin D. In humans, vitamin D exits in two forms—vitamin D2 and vitamin D3. Vitamin D2 (ergocalciferol) is obtained from dietary sources. Two forms of vitamin D can be obtained from dietary sources: vitamin D3 (cholecalciferol) is a 28-carbon molecule derived from the plant sterol ergosterol and humans obtain it from dietary sources. Vitamin D3 is a 27-carbon derivative of cholesterol and is synthesized in the epidermal layer of the skin via exposure to sunlight to cause photodegradation of 7-dehydrocholesterol.

Both forms of vitamin D, the endogenously-synthesized vitamin D3 and the diet-derived vitamin D2, are transported to the liver by proteins—principally the vitamin D binding protein and albumin. In the liver, the vitamin D forms are hydroxylated in the liver into 25OHD2 and 25OHD3, respectively (collectively, 25-hydroxyvitamin D (25OHD)). A further hydroxylation reaction of 25OHD occurs in the kidney to form the active hormone $1,25(OH)_2D$. Production of $1,25(OH)_2D$ is tightly regulated by factors such as parathyroid hormone and phosphorus levels and it has a half-life of only about 4 to 6 hours. In comparison, 25OHD can be stored in muscles and adipose tissue and has a longer plasma half-life of about 2-3 weeks. The plasma concentration of 25OHD is measured as a primary indicator of in vivo vitamin D status.

Methods and assays for determining circulating vitamin D levels as indicated by 25OHD concentration have been developed, including high performance liquid chromatography (HPLC), liquid chromatography-mass spectrometry/mass spectrometry (LC-MS/MS), radioimmunoassay (RIA), chemiluminescent immunoassays (CLIA) and enzyme linked immunoassays (ELISA). There remains significant variability and an unfortunate lack of standardization in assessing vitamin D status (Binkley et al., *J Clin Endocrinol Metab*, 89:3152-3157 (2004)). One of the problems encountered in vitamin D measurement is the hydrophobic nature of 25OHD and to the fact that most of circulating 25OHD is bound to protein, with about 88% of circulating 25OHD bound to vitamin D binding protein (DBP) and about 12% bound to albumin (Hollis, B., *Am J Clin Nutr,* 88:507S-510S, (2008)). Methods for measuring circulating levels of vitamin D and for processing samples for measuring vitamin D levels in a human sample are needed.

Vitamin D is just one example of analytes in vivo that may be bound to a protein that interferes with the ability to detect and/or quantify the analyte. The methods described herein provide a solution for detection of an analyte separate from one or more binding proteins.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

In a first aspect, a method for preparing a sample for analysis is provided. The method comprises providing a processing reagent comprising metaperiodate and contacting a sample suspected of comprising an analyte of interest associated with a protein with the processing reagent to form a mixture. The analyte of interest, if present in the sample (or mixture), is separated from its associated protein for detection of the analyte of interest.

In one embodiment, the method further comprises contacting the sample with a catalyst. In one embodiment, the method further comprises contacting the mixture with a catalyst.

In one embodiment, the catalyst is heat. In an exemplary embodiment, heat is provided to achieve a temperature of the sample or the mixture of above about room temperature (25° C.) and less than about 90° C.

In another embodiment, the catalyst is a metal salt. In an exemplary embodiment, the metal salt is provided in the processing reagent by providing a processing reagent comprising metaperiodate and the metal salt.

In yet another embodiment, the mixture is contacted with a solution comprising the metal salt.

In one embodiment, providing comprises providing a processing reagent comprising a metaperiodate anion associated with a cation of sodium.

In another embodiment, providing comprises providing a processing reagent comprising a metaperiodate anion associated with a cation of sodium and a manganese salt.

In some embodiments, the analyte of interest is a vitamin D metabolite and the protein is vitamin D binding protein.

In other embodiments, the sample is selected from the group consisting of whole blood, plasma and serum.

In another aspect, a method to process and assay a sample is provided. The method comprises contacting a sample suspected of comprising vitamin D or a metabolite of vitamin D with a processing reagent comprising metaperiodate to form a mixture; exposing the mixture to a catalyst; and assaying the mixture to detect vitamin D or vitamin D metabolite in the sample.

In one embodiment, the contacting and the exposing occur sequentially. In other embodiments, the contacting and the exposing occur essentially simultaneously.

In another embodiment, the catalyst is heat. In an exemplary embodiment, heat is applied to achieve a temperature of the sample or the mixture of above about room temperature (25° C.) and less than about 90° C. In another exemplary embodiment, heat is applied to achieve a temperature of the sample or the mixture of between about 40-50° C. for a time of between about 3 to 10 minutes.

In another embodiment, the catalyst is a metal salt. In one exemplary embodiment, the sample is exposed to the metal salt in the contacting step by contacting the sample with a processing reagent comprising metaperiodate and the metal salt. In another exemplary embodiment, the mixture is contacted with a solution comprising the metal salt.

In another embodiment, the catalyst is a metal salt of manganese. By way of non-limiting example, the metal salt is manganese chloride.

In yet another embodiment, contacting comprises contacting the sample with a processing reagent comprising the metaperiodate in the form of a metaperiodate anion intermittently associated with a cation of sodium.

In still another embodiment, the processing reagent comprises between about 0.2 M to about 0.45 M metaperiodate.

In yet another embodiment, contacting comprises contacting the sample with the processing reagent at a ratio of between about 1:2 to 1:12.

The sample, in some embodiments, is selected from the group consisting of whole blood, plasma and serum.

In other embodiments, assaying comprises assaying the mixture by an immunoassay. Exemplary assays, in some embodiments, are enzyme-linked immunosorbent assay (ELISA), radioimmunoassay (RIA) and lateral flow immunoassay.

In one embodiment, the vitamin D metabolite is 25-hydroxy vitamin D (25OHD).

In still another aspect, a method to detect presence of vitamin D or a metabolite of vitamin D in a blood sample is provided. The method comprises combining a blood sample with a solution comprising metaperiodate and manganese to form a mixture and detecting vitamin D or a metabolite of vitamin D in the mixture.

In one embodiment, the sample is combined with the solution at a ratio of between about 1:4 to 1:10 (sample:solution).

In one embodiment, the solution comprises metaperiodate in the form of a metaperiodate anion dissociated periodically from a sodium cation.

In another embodiment, the solution comprises between about 0.2-0.4 M metaperiodate.

In still other embodiments, the solution comprises manganese via preparation from a manganese salt selected from manganese sulfate, manganese chloride or manganese carbonate.

In yet another embodiment, manganese is present in the solution at a concentration of between about 0.5-0.9 mM.

In another embodiment, the solution comprises 0.3M sodium metaperiodate and 0.7 mM manganese chloride.

In another embodiment, the solution comprises 14 mM sodium acetate and the solution pH is adjusted to be between about pH 5-5.5.

In one embodiment, detecting comprises detecting the vitamin D or metabolite of vitamin D using an immunoassay. In another embodiment, the immunoassay is a lateral flow immunoassay comprising a test strip with an antibody for binding to a metabolite of vitamin D.

In another aspect, a kit for processing a sample to separate an analyte of interest from a binding protein, for detection of the analyte of interest separate from the binding protein is provided. The kit comprises one of (i) a container comprising a solution comprising sodium metaperiodate and manganese chloride; or (ii) a first container comprising a solution comprising sodium metaperiodate and a second container comprising manganese chloride; and instructions for use.

The kit, in another embodiment, comprises a solution comprising sodium metaperiodate in an aqueous buffer of sodium acetate.

In another embodiment, the solution comprising sodium metaperiodate has a concentration of sodium metaperiodate of between about 0.1-0.5M.

In still another embodiment, the solution comprising manganese chloride has a concentration of manganese chloride of between about 0.1-1 mM.

In one embodiment, the kit is labelled for use in processing a sample with vitamin D or a metabolite of vitamin D bound to vitamin D binding protein, for detection of vitamin D or a metabolite of vitamin D separate from its binding protein.

In one embodiment, the instructions for use instruct mixing the solution comprising sodium metaperiodate with a sample for detection of vitamin D or a metabolite of vitamin D at a sample to solution ratio of between about 1:2 to 1:15.

In another embodiment, the kit additionally comprises an immunoassay. In one exemplary embodiment, the immunoassay comprises an antibody which binds a vitamin D metabolite. In another embodiment, the immunoassay is a lateral flow immunoassay.

In another aspect, a method of assaying for the presence of vitamin D or a metabolite of vitamin D in a sample is provided. The method comprises adding to a sample obtained from a human or non-human subject an extraction reagent comprising a periodate.

In one embodiment, the periodate is metaperiodate or orthoperiodate. In another embodiment, the periodate is a metaperiodate anion or an orthoperiodate anion associated with a cationic counterion. In one embodiment, the periodate is a metaperiodate anion associated with a cationic counterion selected from sodium ($Na^+$) and potassium ($K^+$).

In one embodiment, the method comprises adding the periodate, particularly metaperiodate, to a sample to form a sample mixture; exposing the mixture to a catalyst; and detecting or measuring the amount of vitamin D or vitamin D metabolite in the sample.

In one embodiment, metaperiodate is a metaperiodate solution having a metaperiodate concentration of between about 0.1-1M, 0.1-0.7M, 0.15-0.6M, 0.2-0.5M or 0.25-0.40M. In another embodiment, the metaperiodate solution has a concentration of between about 0.25-0.35M.

In one embodiment, metaperiodate is added to the sample at a ratio of sample to metaperiodate solution (at a particular metaperiodate concentration) of between about 1:2 to about 1:15 (one part sample to 2 parts metaperiodate solution to about one part sample to 15 parts metaperiodate solution); between about 1:4 to about 1:12; between about 1:4 to about 1:10; or between about 1:4 to 1:8. In another embodiment, the metaperiodate solution is added to the sample to give a mixture that has a sample to metaperiodate solution ratio of about 1:5 1:6, 1:7, 1:8; 1:9 or about 1:10.

In one embodiment, adding metaperiodate or a metaperiodate solution to the sample effects separation of vitamin D from protein to which vitamin D or a metabolite thereof is bound.

In one embodiment, exposing the mixture to a catalyst comprising exposing the mixture to heat, such as by heating the mixture above room temperature (25° C.). In one embodiment, heating the mixture above room temperature comprises heating the mixture to at least about 35° C., 45° C., 55° C. or 65° C. In another embodiment, heating the mixture above room temperature comprises heating the mixture to a temperature above about 35° C., 45° C., 55° C.

or 65° C. In another embodiment, heating the mixture above room temperature comprises heating the mixture to a temperature of between about 35-45° C., 45-55° C., 55-65° C. or 60-70° C.

In one embodiment, the method further comprises maintaining the mixture at room temperature or at a temperature of between about 35-45° C., 45-55° C., 55-65° C. or 60-70° C. for a time period of between about 30 seconds to 30 minutes, between about 1 minute to 10 minutes, between about 1 minute to 5 minutes, between about 5 minutes to 10 minutes, between about 5 minutes to 30 minutes, or between about 1 minute to 20 minutes. In another embodiment, the method further comprises maintaining the mixture at a desired temperature for a time period of at least about 30 seconds, 1 minute, 5 minutes, 15 minutes, 20 minutes, 30 minutes or 60 minutes.

In one embodiment, exposing the mixture to a catalyst comprising exposing the mixture to a metal catalyst that is present in the extraction reagent or that is subsequently added to the mixture. In one embodiment, the metal catalyst is manganese, preferably in the form of a salt.

In a second aspect, a method of assaying for the presence of vitamin D or a vitamin D metabolite in a sample is provided, comprising adding to a sample from a subject a meterperiodate and a metal salt.

In one embodiment, the method comprises mixing the metaperiodate with a metal salt to form a metaperiodate/metal salt solution, then adding the metaperiodate/metal salt solution to the sample to generate the sample mixture.

In one embodiment, the solution comprises metaperiodate at a concentration of about 0.1-2 M, 0.1-1.0 M, 0.1-0.9 M, 0.1-0.7 M, 0.1-0.5 M, 0.1-0.4 M, 0.2-0.4 M. In another embodiment, the solution has a metaperiodate concentration of between about 0.25-0.35 M or 0.27-0.33 M, or has a concentration of about 0.3 M.

In one embodiment, the metaperiodate is added to the sample in a ratio of metaperiodate to sample of about 1:2 to about 1:12 or about 1:8 to 1:12. In another embodiment, the metaperiodate is added to the sample at a ratio of metaperiodate to sample of about 1:10.

In one embodiment, the metal salt is selected from the group consisting of manganese sulphate ($MnSO_4$) and manganese chloride ($MnCl_2$).

In one embodiment, contacting the extractions reagent comprising a metaperiodate and a metal salt with the sample effects separation of an analyte, such as vitamin D, from a binding protein, such as vitamin D binding protein.

In one embodiment, the method further comprises adding a metal ion chelator. In another embodiment, the metal ion chelator is selected from the group consisting of the chelating agent is selected from ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N",N'''-tetraacetic acid, 1,4,7,10-tetraaza-cyclododecane-N,N',N"-triacetic acid, 1,4,7-tris(carboxymethyl)-10-(2'-hydroxypropyl)-1,4,7,10-tetraazocyclodecane, 1,4,7-triazacyclonane-N,N',N"-triacetic acid, 1,4,8,11-tetraazacyclotetra-decane-N,N',N", N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N,N-tetraacetic acid.

In one embodiment, the metal ion chelator is added to the sample mixture such that the concentration in the sample mixture is about 0.1 mM to 2.0 mM, 0.1 mM to 1.0 mM, 0.2 mM to 0.8 mM, 0.4 mM to 0.6 mM, or about 0.5 mM.

In one embodiment, vitamin D or a vitamin D metabolite is the analyte of interest in the sample, and the sample is prepared using the extraction reagent for determination of the concentration of the vitamin D or vitamin D metabolite.

In another embodiment, the sample before and/or after contact with the extraction reagent is not heated. In still another embodiment, the sample is maintained at approximately room temperature or at a temperature between about 20° C. and about 30° C. or at a temperature between 20° C. and 30° C. for about 0 to 5 minutes, 30 seconds to 5 minutes, 1 minute to 5 minutes, 1 minute to 10 minutes, or 5 minutes to 10 minutes. In another embodiment the sample and or mixture is maintained at approximately room temperature or at a temperature between about 20° C. and about 30° C. for less than about 1 minute, 5 minutes, 10 minutes, 15 minutes or 20 minutes, prior to detecting the vitamin D or vitamin D metabolite.

In one embodiment, after mixing the metaperiodate or metaperiodate-manganese solution to the sample to generate a mixture, the mixture is maintained at approximately room temperature; that is, the mixture is not heated as part of the sample processing.

In one embodiment, the detecting or measuring comprises performing an immunoassay. In another embodiment, no protein-removal step is performed prior to performing the immunoassay; that is, the protein(s) separated from the analyte of interest is (are) not removed from the mixture prior to detecting or measuring using an immunoassay.

In one embodiment, the detecting or measuring comprises performing an immunoassay selected from the group consisting of ELISA (enzyme-linked immunosorbent assay), RIA (radioimmunoassay), FIA (fluorescence immunoassay), LIA (luminescence immunoassay), or ILMA immunoluminometric assay. In still another embodiment, the detecting or measuring comprises performing a solid phase immunofluorescence assay or a lateral flow immunochromatographic assay.

In one embodiment, the detecting or measuring comprises applying the mixture to a lateral flow strip. In another embodiment, the lateral flow strip comprises reagents for detecting the vitamin D or metabolite of vitamin D. In still another embodiment, the lateral flow strip comprises an immunoglobulin that specifically binds to 25OHD. In yet another embodiment, the immunoglobulin does not bind a vitamin D binding protein. In another embodiment, the immunoglobulin does not bind 24,25$(OH)_2$D and/or 25,26 $(OH)_2$D. In another embodiment, the immunoglobulin is an antibody or fragment thereof. In still another embodiment, the antibody is a polyclonal or a monoclonal antibody.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE FIGURES

FIG. 2A is a graph of RFU signal/background ratio (S/B) from an instrument detection of vitamin D metabolite 25OHD$_3$ as a function of concentration of vitamin D metabolite 25OHD$_3$, in ng/mL, introduced into human serum at the indicated concentrations, and the samples were processed at 55° C. using a processing reagent with metaperiodate for 4 minutes (diamonds), 6 minutes (squares), 8 minutes (triangles), 12 minutes (x symbols) and 14 minutes (* symbols);

FIG. 2B is a bar graph of RFU signal/background ratio (S/B) from an instrument detection of vitamin D metabolite 25OHD$_3$ as a function of concentration of vitamin D metabolite 25OHD$_3$, in ng/mL, introduced into human serum at the indicated concentrations (6.1 ng/mL, 17.6 ng/mL, 33.4 ng/mL and 97.4 ng/mL), and the samples were processed at 55° C. using a processing reagent with metaperiodate for, 8 minutes (open bars), 12 minutes (dotted fill) and 14 minutes (cross hatch fill);

DETAILED DESCRIPTION

Figure 1A:
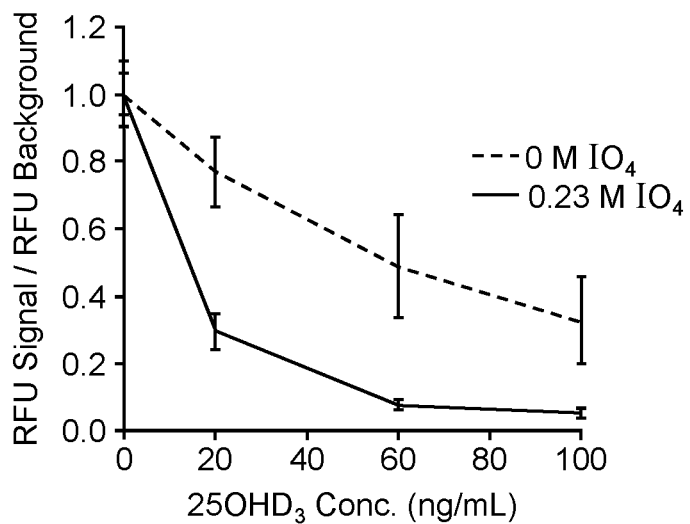
FIGS. 1A-1B are graphs of RFU signal/background ratio (S/B) from an instrument detection of vitamin D metabolite 25OHD$_3$ as a function of concentration of vitamin D metabolite 25OHD$_3$, in ng/mL, in an albumin solution (FIG. 1A) and in human serum (FIG. 1B) in which a vitamin D metabolite 25OHD$_3$ was added at the indicated concentration, and the samples were processed using a processing reagent with metaperiodate (solid line) or without metaperiodate as a negative (dashed line)

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

"Absorbent material" as used herein refers to material used in devices and assays that allows and promotes fluid flow through the device, assay, or members in a device or assay. Exemplary materials include those described in, e.g., U.S. Pat. No. 4,632,901, such as, for example, fibrous materials such as cellulose acetate fibers, cellulose or cellulose derivatives, polyester, or polyolefin.

"Antibody" or "immunoglobulin" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

"Analyte" or "analyte of interest" refers to a compound to be detected or measured. The analyte can be any substance for which there exists an analyte binding member or for which an analyte binding member can be prepared, e.g., carbohydrate and lectin, hormone and receptor, complementary nucleic acids, and the like. The analyte binding member can be specific or non-specific. Analytes include virtually any compound, composition, aggregation, or other substance which may be immunologically detected. That is, the analyte, or portion thereof, will be antigenic or haptenic having at least one determinant site, or will be a member of a naturally-occurring binding pair. An analyte of interest is a vitamin D (e.g., vitamin $D_2$ or vitamin $D_3$) or a metabolite of vitamin D, such as 25-hydroxyvitamin $D_2$ (25OHD$_2$) and 25-hydroxyvitamin $D_3$ (25OHD$_3$), or the two metabolites collectively, referred to herein as 25-hydroxyvitamin D (25OHD)).

"Label reagent" refers to a substance comprising a detectable label attached with a specific binding member. The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the test device at a site upstream from the capture zone, it can be combined with the fluid sample to form a fluid solution, it can be added to the test strip or device separately from the test sample, or it can be predeposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. The label can produce its signal through either chemical or physical means. Examples include enzymes and substrates, chromogens, catalysts, fluorescent compounds, chemiluminescent compounds, and radioactive labels. Other labels include colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in a sample without the need for additional signal producing components at the detection sites.

The term "periodate" includes both periodate and periodic acid. This term also includes both metaperiodate ($IO_4^-$) and orthoperiodate ($IO_6^{5-}$) as well as the various salts of periodate, such as sodium periodates and potassium periodates.

As used herein, the term "specifically binds" refers to the binding specificity of a specific binding pair. "Specific pair binding member" refers to a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (anti-ligand), specific binding pair member and specific binding pair partner, and the like. A molecule may also be a specific binding pair member for an aggregation of molecules; for example, an antibody raised against an immune complex of a second antibody and its corresponding antigen may be considered to be a specific binding pair member for the immune complex.

II. Methods of Sample Processing

In a first aspect, a method for preparing a sample is provided. Typically, and in some embodiments, the sample is subjected to a subsequent analytical procedure. The method thus provides an approach to process a sample for analysis of a component in the sample. In the method, a processing reagent, also referred to herein as an extraction reagent, is combined, mixed or brought into contact with a sample comprising (or suspected of comprising) an analyte of interest that is associated with or bound to a protein. The method is particularly suited for use for analytes of interest whose detection is complicated by or impaired by the presence of the protein. In situations where a binding protein interferes with detection of an analyte of interest, the method described herein finds utility. To exemplify the method, the working examples detail use of the method in a sample comprising a metabolite of vitamin D bound by vitamin D binding protein; however, it will be appreciated that the method is not limited to this analyte-protein pair. For example, steroid hormones, retinol, and mRNAs are transported in vivo bound to plasma proteins—for example, cortisol-binding globulin, retinol binding protein, sex hormone-binding globulin, polyadenylate binding protein—and the method described herein is applicable.

In the method, a processing reagent comprising a periodate is provided, and is combined with the sample suspected of comprising an analyte of interest associated with a protein. Components in the processing reagent and/or processing of the mixture of the processing reagent and sample effect separation of the protein from the analyte of interest, permitting detection of the analyte of interest, if present in the sample (or mixture) separate from its associated protein. The processing reagent and its use are detailed in Section A below.

In another aspect, a method to process and assay a sample is provided. The method comprises contacting a sample comprising or suspected of comprising an analyte of interest that is associated with a binding protein with a processing reagent comprising a periodate to form a mixture. The mixture is exposed to a catalyst, simultaneously with or sequentially to the contacting of the sample and the processing reagent. The mixture is then assayed to detect the analyte of interest in the sample (or mixture). Assays and detection of a metabolite of vitamin D as a model for the method are set forth in Section B below.

A. Processing Reagent to Dissociate an Analyte from a Binding Protein

The processing reagent for use in the methods described herein comprises a periodate. In one embodiment, the periodate is metaperiodate. The processing reagent and the sample to be processed are contacted, for example, by mixing or combining the two in a suitable container. A catalyst is provided and is contacted with the processing reagent, the sample, or the combination of the processing reagent and the sample. Contact of the sample and the processing reagent effects separation of a binding protein from the analyte of interest.

The processing reagent comprises a periodate, which is an anion composed of iodine and oxygen and exists in two forms: metaperiodate ($IO_4^-$) and orthoperiodate ($IO_6^-$). In some embodiments, the periodate is a salt, such as sodium metaperiodate ($NaIO_4$) or sodium orthoperiodate ($Na_2H_3IO_6$) or potassium periodate ($KIO_4$). In studies described herein, a metaperiodate is exemplified, and in particular sodium metaperiodate in an aqueous solution, such as water or a buffer. The sodium metaperiodate when in an aqueous solution is comprised of a metaperiodate anion and a sodium cation, that are intermittently associated and disassociated to a degree that is based on solubility of the salt in the aqueous solution, as is common for salts in an aqueous medium.

In one embodiment, the processing reagent comprises a metaperiodate at a concentration of between about 0.1 M to 0.4 M, 0.2 M to 0.7 M, 0.3 M to 0.6 M, or 0.4 M to 0.5 M. In other embodiments, the processing reagent comprises metaperiodate at a concentration of about 0.1-2 M, 0.1-1.0 M, 0.1-0.9 M, 0.1-0.7 M, 0.1-0.5 M, 0.1-0.4 M, 0.2-0.4 M. In another embodiment, the metaperiodate in the processing reagent has a concentration of at least about 0.15 M or 0.20 and less than about 0.50M or 0.45M or 0.40M or 0.35M. In another embodiment, the processing reagent comprises a metaperiodate salt at essentially its saturation solubility in the aqueous medium of the reagent, whether that medium is water or a buffer. In a specific embodiment, the processing reagent comprises or consists essentially of 0.3M metaperiodate in 14 mM sodium acetate at pH 5-5.5. A solution comprising metaperiodate for mixing with a sample in preferred embodiments has a concentration of metaperiodate of between about 0.25-0.35 M or 0.27-0.33 M, or has a concentration of about 0.3 M. It will be appreciated that metaperiodate salt is dry form can be added directly to a liquid sample (e.g., blood, urine) to form a mixture of sample and metaperiodate.

In one embodiment, the aqueous medium of the processing reagent is water or a buffer, and in a one embodiment the buffer is a sodium acetate buffer. In the studies described herein, the sodium acetate was at a concentration of 14 mM, with a pH adjusted to be between about 5.0-5.5. In one embodiment, the processing reagent comprises a metaperiodate salt in a buffer, and in another embodiment, the processing reagent comprises a metaperiodate salt in an acetate buffer. In one embodiment, the processing reagent comprises a buffer with a pH adjusted to between about 4.5-6.5, or between about 4.8-6.0 or between about 4.9-5.8.

In the method, the sample and processing reagent are exposed to a catalyst. The catalyst exposure can occur simultaneously with contact of the sample and the processing reagent, for example by including the catalyst as a component of the processing reagent. Alternatively, the catalyst exposure can occur sequentially to contact of the sample and the processing reagent by exposing the mixture of the sample and the processing reagent to the catalyst. Both approaches are detailed below.

In one embodiment, the catalyst is heat. The sample and the processing reagent are, in one version of the embodiment, brought into contact to form a mixture, and heat is applied to the mixture. Alternatively, the sample, the processing reagent, or both are heated prior to their being combined into a mixture, to achieve the catalytic effect of heat on the mixture by application of the heat to one or both of the individual components. Heat as a catalyst can be applied to provide a temperature of the sample or of the mixture of above about room temperature (25° C.) and less than about 90° C. In another embodiment, the mixture is heated to a temperature of between about 25-37° C., 25-45° C., 25-50° C., or 25-60° C. In one embodiment, heating the mixture above room temperature comprises heating the mixture to at least about 35° C., 45° C., 55° C. or 65° C. In another embodiment, heating the mixture above room temperature comprises heating the mixture to a temperature above about 30° C., 40° C., 45° C., 55° C. or 65° C. In another embodiment, heating the mixture above room temperature comprises heating the mixture to a temperature of between about 35-45° C., 45-55° C., 55-65° C. or 60-70° C.

In another embodiment, the mixture is held at a temperature in these ranges for a period of between about 1 minute to 20 minutes, 2 minutes to 15 minutes, 3 minutes to 10 minutes or for at least about 1 minute, 3 minutes, 5 minutes, 10 minutes, 15 minutes or 20 minutes.

In another embodiment, the catalyst is a metal salt. A catalyst in the form of a metal salt can be added to the processing reagent, or the metal salt (neat or as an aqueous solution of metal salt) can be added to the mixture or the sample. In the case where the metal salt is a component of the processing reagent, exposure to the catalyst occurs simultaneously with contact of the sample and the processing reagent. In the case where the metal salt is added to the mixture of sample and processing reagent composed of a metaperiodate solution, exposure to the catalyst occurs sequentially to contact of the sample and the processing reagent.

An exemplary metal salt as a catalyst is a manganese salt. Manganese with an oxidation state of +2 is preferred, such as in manganese sulfate, manganese chloride and manganese carbonate.

In one embodiment, the processing reagent comprises a manganese salt at a concentration of between about 0.1-2.0 mM, 0.1-1 mM, 0.2-1.0 mM, 0.2-0.8 mM, 0.3-0.9 mM, or 0.5-0.8 mM. In another embodiment, the manganese salt in the processing reagent has a concentration of at least about 0.15 M or 0.20 mM and less than about 0.50 mM or 0.45 mM or 0.40 mM or 0.35 mM. In one embodiment the processing reagent comprises or consists essentially of 0.3M metaperiodate and 0.7 mM $MnCl_2$ in 14 mM sodium acetate at pH 5-5.5.

The processing reagent (or extraction reagent) composed of a metaperiodate (or periodate) salt in a buffer is combined, mixed or brought into contact with a sample comprising (or suspected of comprising) an analyte of interest that is associated with or bound to a protein. The processing reagent and the sample when combined, mixed or contacted form a mixture. The mixture is exposed to a catalyst, which as described above, can occur simultaneously with the combining, mixing or contacting of the sample and the processing reagent, or can occur after formation of the mixture. The binding protein and the analyte of interest are separated from one another, to permit analysis of the analyte of interest separate from the binding protein.

In one embodiment, processing reagent is added to the sample at a ratio of sample to processing reagent (having a particular metaperiodate concentration and/or manganese concentration) of between about 1:2 to about 1:15 (one part sample to 2 parts processing reagent to about one part sample to 15 parts processing reagent); between about 1:4 to about 1:12; between about 1:4 to about 1:10; or between about 1:4 to 1:8. In another embodiment, the processing reagent is added to the sample to give a mixture that has a sample to processing reagent ratio of about 1:5 1:6, 1:7, 1:8; 1:9 or about 1:10.

The sample provided for processing can be any sample from a human or non-human subject, including but not limited to whole blood, serum, plasma, urine, mucus and the like.

In some embodiments, a metal ion chelator is added to the mixture comprised of sample and processing reagent that comprises a metal salt to render inactive the activity of the metal salt. The metal ion chelator can be a divalent metal ion chelator, such as ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodec-ane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid. By adding the chelator, the effect of the manganese to activate metaperiodate is attenuated or halted. The ion chelator can be added to the mixture or can be a component in the immunoassay, as illustrated below where EDTA is added to the sample zone of a lateral flow immunoassay. In one embodiment, the metal ion chelator is present in the method by addition to the mixture of sample and processing reagent, such that the concentration of ion chelator in the mixture is between about 0.1-2.0 mM, 0.1-1.0 mM, 0.2-0.8 mM, or 0.4-0.6 mM. In other embodiments, the concentration of ion chelator present in the method, mixture, or immunoassay is between about 0.45-0.55 mM or 0.47-0.52 mM.

B. Optional Detection of the Analyte of Interest

In some embodiments and aspects, a sample that is treated with the processing reagent described above is analyzed to ascertain presence or quantity of an analyte of interest. The analyte of interest subsequent to exposure to the processing reagent and any optional incubation period is separate from proteins and available for detection. A variety of detection approaches are contemplated and will vary according to the analyte of interest. Some examples are now described.

In an immunoassay, specific or partially specific binding by an antibody or antibody fragment to the analyte of interest is utilized. Radioimmunoassays (RIA) may be used in which a known amount of the analyte of interest is labeled with a radioactive isotope and competes with the same analyte in the sample for binding to an antibody specific for the analyte. RIAs are well known to the ordinary skilled artisan. While RIAs are very sensitive, simple, and reliable, the use of radioactivity limits such detection assays to highly qualified laboratories equipped to deal with safety and waste issues pertaining to use of radioactive reagents. Other sensitive and reliable detection methods include various luminescence-based immunoassays (LIAs), fluorescence immunoassays (FIAs) including immunoluminometric assays (ILMAs), and enzyme-linked immunosorbent assays (ELISAs). These assays may be direct, wherein the antibody which binds the analyte of interest is directly attached or linked to a detection moiety, or indirect, wherein the antibody which binds the analyte of interest is bound during the assay by a secondary antibody which is linked to the detection moiety. The detection moieties are well known to the ordinarily skilled artisan and include but are not limited to the use of chemiluminescence moieties such as acridinium esters and derivatives of isoluminol, or a bioluminescence detection moiety such as luciferase. Direct labels may include fluorescent or luminescent tags, metals, dyes, radionuclides, and the like, attached to the antibody. Indirect labels may include various enzymes well known in the art, such as alkaline phosphatase, horseradish peroxidase and the like. Also contemplated are competitive binding assays and western blotting. In these assays, specific immunological binding of the antibody to the analyte can be detected directly or indirectly. All such assay methods are well known to the ordinary skilled artisan.

In the illustrative embodiment herein, an immunoassay for detection of vitamin D or a metabolite thereof are described. Antibodies which specifically bind to vitamin D or a vitamin D metabolite are known in the art (see, for example, U.S. Pat. Pub. No. 2013/0059825). Antibodies which specifically bind the vitamin D metabolite 25OHD are found in commercially available kits including DiaSorin LIAISON®, Siemens Healthcare Diagnostics ADVIA®, Abbott Diagnostics ARCHITECT®, and Roche Diagnostics ELECSYS®. In one embodiment, a monoclonal antibody which can detect both 25-OH D2 and D3 is used (e.g., a sheep monoclonal antibody obtained from Bioventix® ("Total 25-Hydroxy D2+D3"; "VitD3.5H10").

In one embodiment, an enzyme-linked immunosorbent assay (ELISA) is performed with the sample subsequent to processing as described above. In such an assay, for example, samples are typically incubated in the presence of an immobilized first specific binding agent (e.g. an antibody) capable of specifically binding the biomarker. Binding of the biomarker to the first specific binding agent may be measured using any one of a variety of known methods, such as using a labeled second specific binding agent capable of specifically binding the biomarker (at a different epitope) or the first specific binding agent.

The use of immobilized antibodies or fragments thereof specific for the analyte of interest in an immunoassay for use in the methods described herein is contemplated. Antibodies can be immobilized onto a variety of solid supports, such as magnetic or chromatographic matrix particles, a bead (such as a colloidal particle, nanoparticle, or latex bead), the surface of an assay plate (such as microtiter wells), pieces of a solid substrate material (such as plastic, nylon, paper), and the like. In certain embodiments, the solid support comprises metal, glass, a cellulose-based material (e.g., nitrocellulose), or a polymer (e.g., polystyrene, polyethylene, polypropylene, polyester, nylon, polysulfone, etc.).

B1. Illustrative Examples: Preparation of Sample Comprising a Vitamin D Metabolite and Detection Thereof For Purposes of Illustrating the Methods of Processing a Sample and of Methods for processing and analyzing a sample, studies were conducted using a processing reagent as described herein with samples comprising a metabolite of vitamin D. The processed samples were analyzed to detect the vitamin D metabolite free from any binding protein(s). These studies, and the methods of processing a sample, are now described.

Vitamin D is a steroid hormone involved in intestinal absorption of calcium and regulation of calcium homeostasis. Vitamin D is essential for the formation and maintenance of strong, healthy bones. Interest in monitoring vitamin D levels is increasing as researchers uncover links between vitamin D and conditions such as heart disease, diabetes, rheumatoid arthritis, multiple sclerosis, Parkinson's disease and some cancers. As these studies become public, clinical laboratories experience an increased demand for vitamin D testing.

As noted above, in humans, vitamin D exits in two forms—vitamin D2 and vitamin D3. Both forms of vitamin D, the endogenously-synthesized vitamin D3 and the diet-derived vitamin D2, are transported to the liver by proteins—principally the vitamin D binding protein and albumin. In the liver, the vitamin D forms are metabolized (hydroxylated) in the liver into 25OHD2 and 25OHD3, respectively (collectively, the metabolite 25-hydroxyvitamin D (25OHD)). A further hydroxylation reaction of 25OHD occurs in the kidney to form the active hormone 1,25(OH)$_2$D (also a metabolite of Vitamin D).

In a first study, described in Example 1, separation of vitamin D metabolite from its binding protein using a processing reagent as described herein was investigated. A processing reagent comprising sodium metaperiodate (NaIO$_4$) in water was prepared. Model samples were prepared by spiking an aqueous albumin solution and human serum with a vitamin D metabolite (25OH D3). The samples were mixed with the processing reagent an incubated at room temperature. The processed samples were then assayed for, vitamin D metabolite using an immunoassay test device with an antibody for the vitamin D metabolite attached to fluorescent label. The immunoassay test device is a competitive inhibition immunoassay using vitamin D metabolite bound to fluorescent particles in the immunoassay competing with vitamin D metabolite in the sample for binding with an antibody for vitamin D metabolite. Detection of the fluorescent particles in a capture or test zone on the immunoassay was ascertained using a commercially-available instrument with an optical system for detection of fluorescent signal (Sofia® Analyzer, from Quidel Corporation), so as vitamin D concentration in the sample increases signal is inhibited. Results are presented in Tables 1A-1B (below in Example 1) and in FIGS. 1A-1B.

Figure 1B:
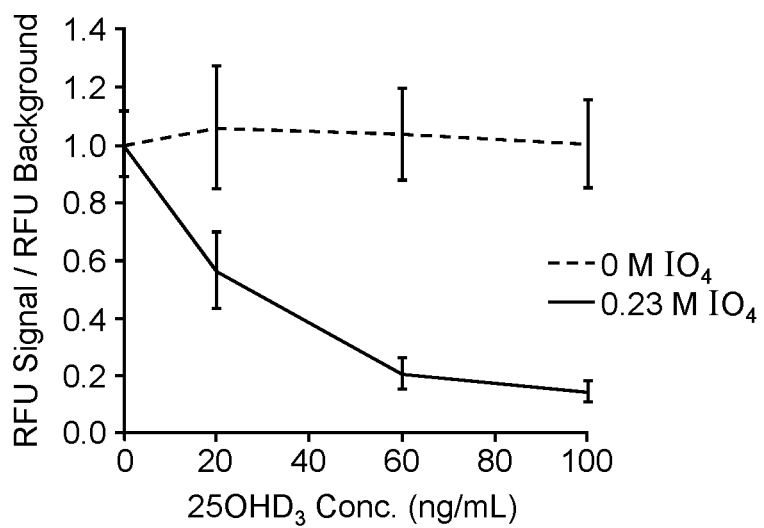

FIGS. 1A-1B are graphs of RFU signal/background ratio (S/B) from the instrument detection of vitamin D metabolite 25OHD$_3$ as a function of concentration of vitamin D metabolite 25OHD$_3$, in ng/mL. FIG. 1A shows the results for the samples of albumin solution and FIG. 1B shows the results for the samples of human serum. Albumin samples processed with a processing reagent with metaperiodate (solid line, FIG. 1A) show the metaperiodate interacts with the albumin (which is known to bind 25OH D3) to improve detection of the vitamin D metabolite (a decrease in signal (relative fluorescent units) indicates an increase in quantity of analyte detected as a competitive inhibition immunoassay format was used). In addition, the processing reagent treatment allowed for detection of the vitamin D metabolite analyte in human serum (solid line, FIG. 1B), whereas absent treatment with the processing reagent the metabolite was not detectable (dashed line, FIG. 1B). These data indicate that the processing reagent extracts the analyte of interest from proteins to which it is bound, e.g., albumin and/or vitamin D binding protein, that normally sequester the vitamin D 25OH D3 analyte. Sodium (ortho)periodate and sodium (para)periodate were also tested as described above, and both showed the ability to extract vitamin D.

In another study, described in Example 2, heat as a catalyst in the method was evaluated. Samples of human serum with known vitamin D3 metabolite concentrations were processed using a processing reagent comprising metaperiodate by combining the sample and processing reagent at a 1:8 ratio to form a mixture. The mixtures were heated to a test temperature (25° C., 37° C., 40° C., 55° C., 65° C., 75° C. and 85° C.) for a time period of 4 minutes, 6 minutes, 8 minutes, 12 minutes or 14 minutes. The concentration of vitamin D3 metabolite in the processed samples was measured using an optical reader. Results for the samples processed using a 55° C. temperature (as representative of the data) are shown in Table 2 (Example 2 below) and in FIGS. 2A-2B.

FIG. 2A is a graph showing the RFU signal/background ratio (S/B) as a function of concentration of vitamin D metabolite 25OHD$_3$, in ng/mL, for the samples processed for at 55° C. using a processing reagent with metaperiodate for 4 minutes (diamonds), 6 minutes (squares), 8 minutes (triangles), 12 minutes (x symbols) and 14 minutes (* symbols). FIG. 2B is a bar graph of RFU signal/background ratio (S/B) from an instrument detection of vitamin D metabolite 25OHD$_3$ as a function of concentration of vitamin D metabolite 25OHD$_3$, in ng/mL, introduced into human serum at the indicated concentrations (6.1 ng/mL, 17.6 ng/mL, 33.4 ng/mL and 97.4 ng/mL) for the samples processed at 55° C. using a processing reagent with metaperiodate for, 8 minutes (open bars), 12 minutes (dotted fill) and 14 minutes (cross hatch fill). This study revealed that time and temperature both impact the extraction efficiency. For detection using an immunoassay post sample processing, both are factors to vary to tailor extraction of the analyte from its binding protein.

Figure 3:
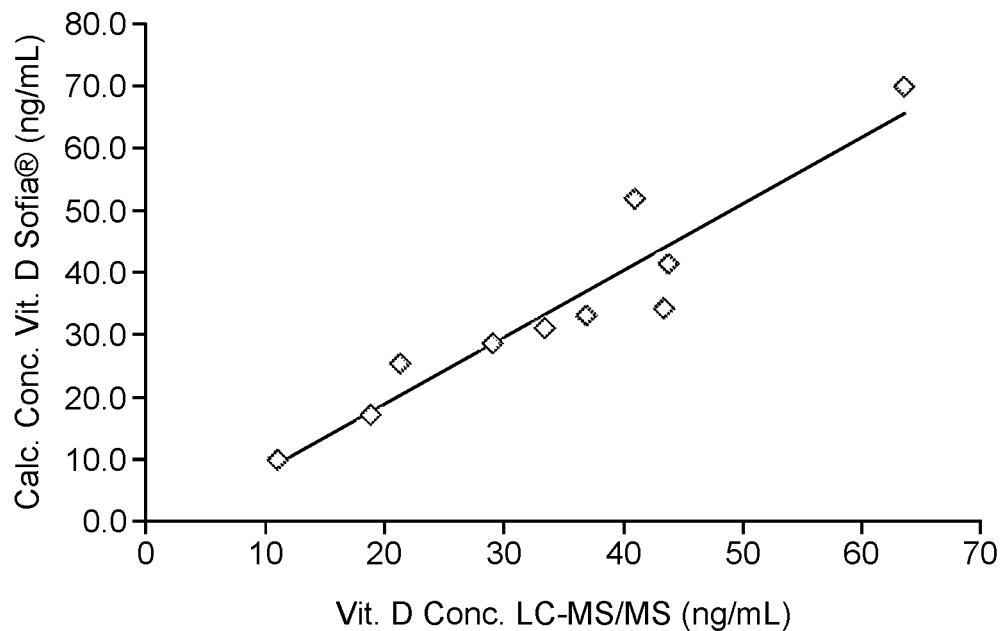
FIG. 3 is graph showing the correlation of vitamin D metabolite calculated concentration, in ng/mL, in samples processed with a processing reagent comprising metaperiodate, at a sample to processing reagent ratio was 1:8 and incubated for 10 minutes at 55° C. measured and analyzed using a competitive inhibition immunoassay with fluorescent particles read using an optical fluorescent reader instrument (SOFIA®) plotted against the vitamin D3 metabolite concentration, in ng/mL, in each sample without processing measured by LC-MS/MS.

In another study, processing reagents with various concentrations of metaperiodate between 0.1M to 0.6 M IO$_4$ were prepared. Samples of vitamin D metabolite in human serum were processed, as described in Example 3, by contacting the sample with the processing reagent at various ratios of sample:processing reagent from 1:1 to 1:15. The mixtures were heated to 55 C and incubated for 10 minutes, and the vitamin D concentration was measured using an immunoassay (competition inhibition format) and optical analysis. Samples unprocessed with the processing reagent were analyzed via LC-MS/MS to determine vitamin D metabolite concentration in the sample. FIG. 3 shows the correlation between the two analysis methods for the sample processed at a 1:7 sample to processing reagent ratio. The processed sample yields an accurate measure of analyte concentration, given the correlation (r=0.896) with the LC-MS/MS analysis.

Example 4 describes a study where extraction of vitamin D metabolite from samples of whole blood, serum and plasma was conducted. Using an extraction reagent (also referred to herein as processing reagent) comprising metaperiodate and heat as a catalyst, vitamin D concentrations in the processed samples were measured using a competitive inhibition immunoassay test strip read using optical fluorescent reader instrument (SOFIA®). The vitamin D concentration in unprocessed samples (samples not treated with the extraction reagent) was analyzed by LC-MS/MS to compare accuracy of the concentration measurement obtained from the processed samples.

Figure 4A:
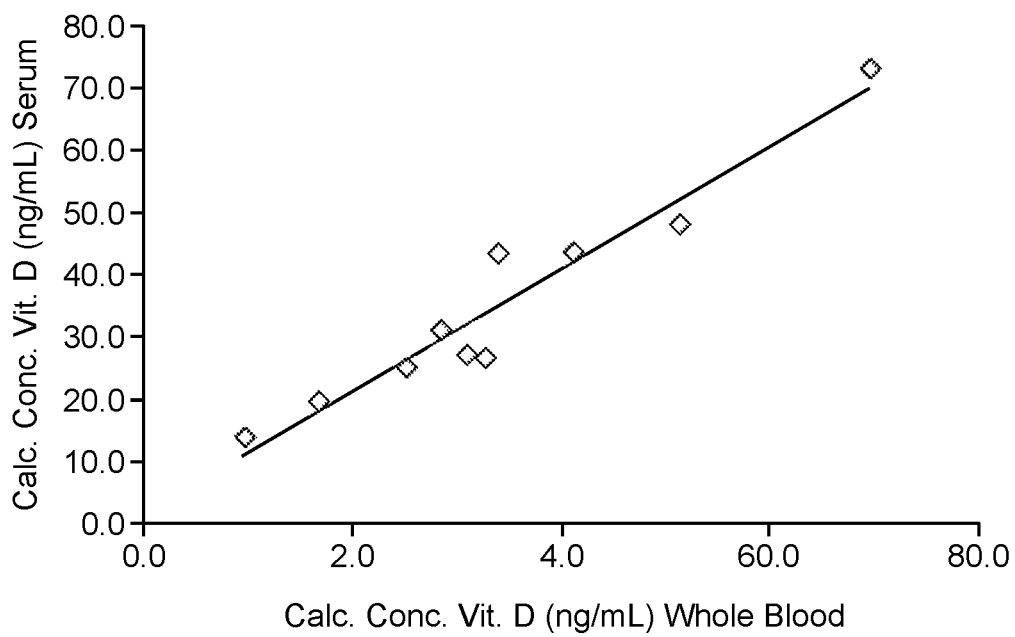
FIG. 4A is graph showing the correlation of the calculated vitamin D metabolite concentration, in ng/mL, in human serum samples (Y-axis) and in human whole blood samples (x-axis), the samples processed in the same manner and measured for vitamin D metabolite concentration using an optical fluorescent reader instrument (SOFIA®)
Figure 4B:
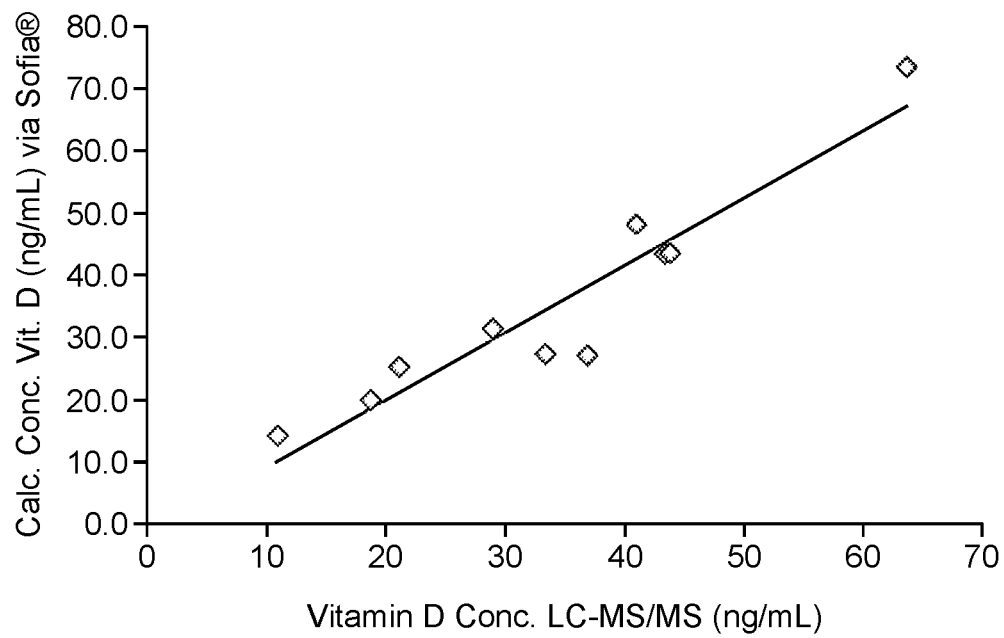
FIG. 4B is graph showing the correlation of the calculated vitamin D metabolite concentration, in ng/mL, in whole blood samples comprising vitamin D metabolite, the metabolite measured using an optical fluorescent reader instrument (SOFIA®), where the samples comprise vitamin D metabolite in human whole blood and were processed with a processing reagent comprising metaperiodate, where the sample to processing reagent ratio was 1:8, and the mixture of sample/processing reagent was incubated for 10 minutes at 55° C. to the vitamin D metabolite concentration in the samples without processing and measured by LC-MS/MS.

FIG. 4A is graph showing the correlation of the vitamin D metabolite concentration, in ng/mL, in human serum samples (y-axis) and in human whole blood samples (x-axis) from samples processed with the extraction reagent, applied to the immunoassay test strip and detection of fluorescent particles with vitamin D bound thereto with the fluorescent reader instrument (SOFIA®). A strong correlation (r=0.9325) was observed. FIG. 4B is graph showing the correlation of the calculated vitamin D metabolite concentration, in ng/mL, in whole blood samples processed and analyzed as described compared to the vitamin D metabolite concentration in the unprocessed samples as measured by LC-MS/MS. A strong correlation (r=0.8922) was observed.

In other studies, chemical catalysts of the method for processing samples using the processing reagent comprising a periodate were evaluated. As described in Example 5, metal salts as catalysts in the processing reagent were investigated, using manganese salts as exemplary. A processing reagent comprising metaperiodate and manganese sulfate (MnSO$_4$) was prepared. A serum sample comprising vitamin D metabolite was contacted with the processing reagent comprising the metaperiodate and manganese sulfate and a processing reagent with metaperiodate absent manganese sulfate. Extent of vitamin D metabolite extraction at room temperature was evaluated over a 30 minute test, and the results are shown in FIG. 5.

Figure 5:
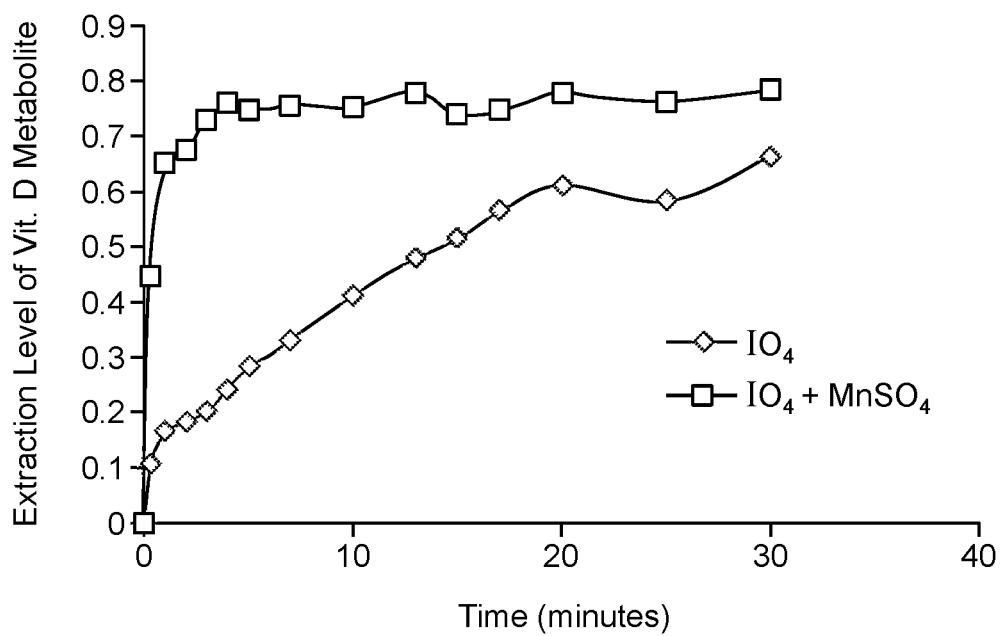
FIG. 5 is a graph of extent of extraction of vitamin D metabolite from its binding protein in human serum samples processed with a processing reagent comprising metaperiodate (diamonds) or a processing reagent comprising metaperiodate and manganese sulfate (squares) as a function of time, in minutes.

FIG. 5 shows the extent of extraction of vitamin D metabolite from its binding protein in human serum samples processed with both processing reagents—the reagent comprising metaperiodate only (diamonds) and the processing reagent comprising metaperiodate and manganese sulfate (squares). Addition of the metal salt ($MnSO_4$) increased the rate of the reaction that separates the analyte of interest from its binding protein.

Processing reagents comprising manganese chloride ($MnCl_2$) as a chemical catalyst were also studied. Example 6 describes a study where processing reagents with metaperiodate at concentrations between 0.195 M and 0.4 M with manganese chloride at manganese concentrations between 0.2 mM to 0.6 mM were prepared. Human blood, serum and plasma samples with vitamin D metabolite were prepared, and mixed with the processing reagents at ratios (sample to processing reagent) of between 1:4 and 1:16. Extraction of vitamin D from the proteins in the blood, serum and plasma was evaluated by analyzing the samples for vitamin D concentration using a competitive immunoassay test strip and optical fluorescent reader. Data for samples processed with an extraction reagent comprised of 0.22M metaperiodate, 0.5 mM manganese (as manganese chloride) and a sample:extraction reagent ratio of 1:10 are shown in FIGS. 6A-6B.

Figure 6A:
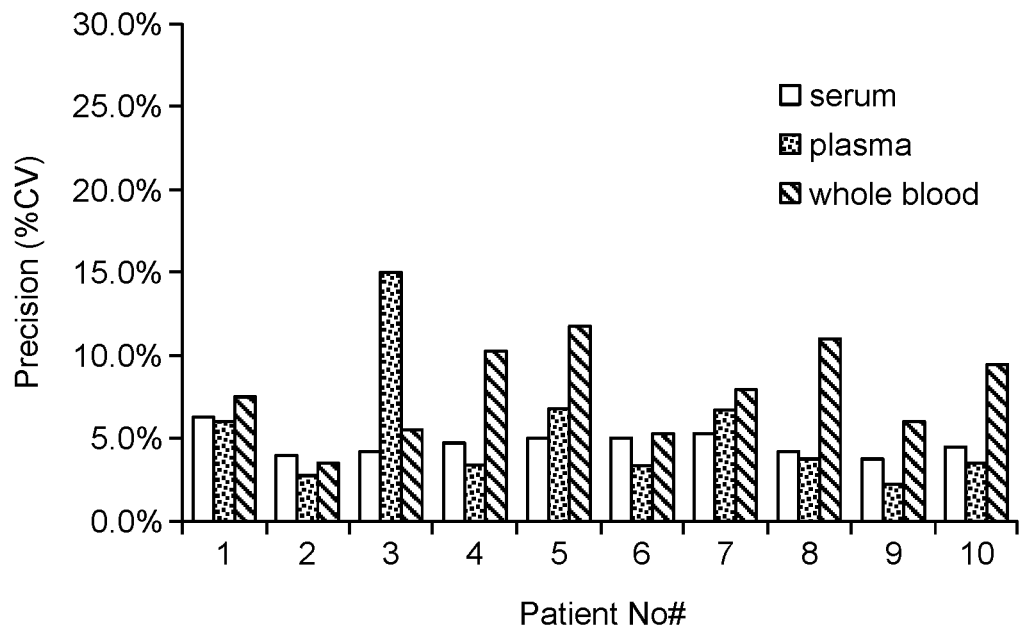
FIG. 6A is a bar graph showing precision, as a percent coefficient of variation (% CV), of the measured concentrations of vitamin D metabolite in serum (open bars), plasma (dashed fill) and whole blood (cross hatch fill) from ten human patient samples, each sample processed with a reagent comprising metaperiodate and manganese chloride, at a sample to reagent dilution ratio of 1:10.

FIG. 6A is a bar graph showing precision, as a percent coefficient of variation (% CV), of the measured concentrations of vitamin D metabolite in serum (open bars), plasma (dashed fill) and whole blood (cross hatch fill) from ten human patient samples, each sample processed with the processing reagent noted in the preceding paragraph. For the ten patient samples, the measured concentrations of vitamin D metabolite in the whole blood, serum and plasma of each patient sample was good, typically with a percent CV of less than 10% and usually less than 5%.

Figure 6B:
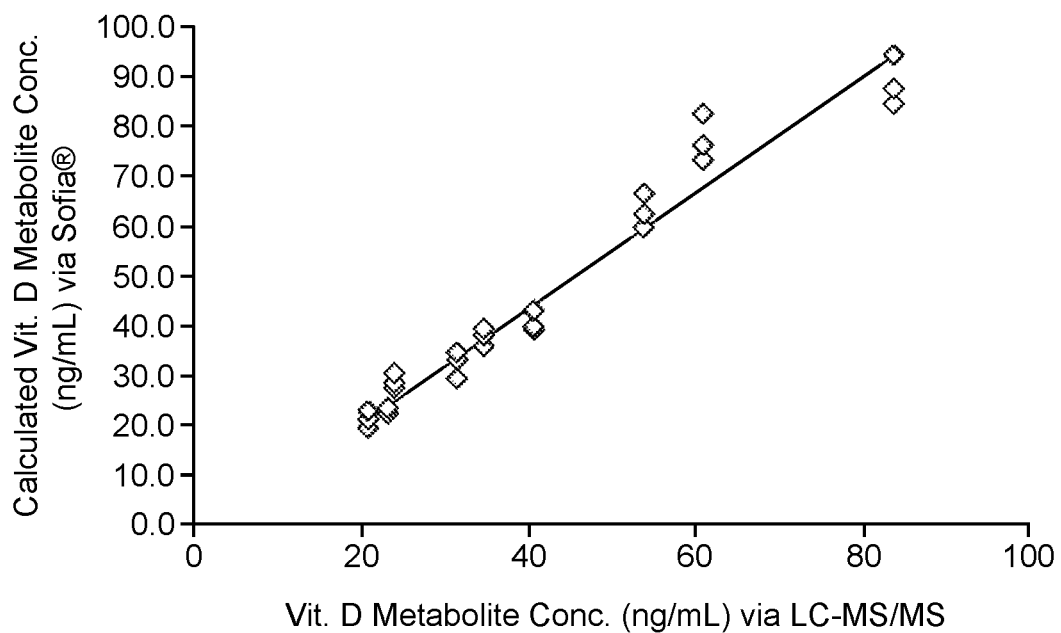
FIG. 6B is a graph showing the correlation of the calculated vitamin D metabolite concentration, in ng/mL, in the serum, plasma and whole blood samples comprising vitamin D metabolite, the metabolite measured using an optical fluorescent reader instrument (SOFIA®) where the samples were processed as noted in FIG. 6A, to the vitamin D metabolite concentration in the samples without processing and measured by LC-MS/MS.

FIG. 6B shows the accuracy of the vitamin D concentrations measured in the samples processed with the processing reagent and then analyzed using the immunoassay, compared to an aliquot of the each sample not processed and analyzed for vitamin D concentration via LC-MS/MS. The correlation was high (r=0.956) indicating the accuracy of the measured analyte concentrations when processed according to the claimed methods.

Figure 7:
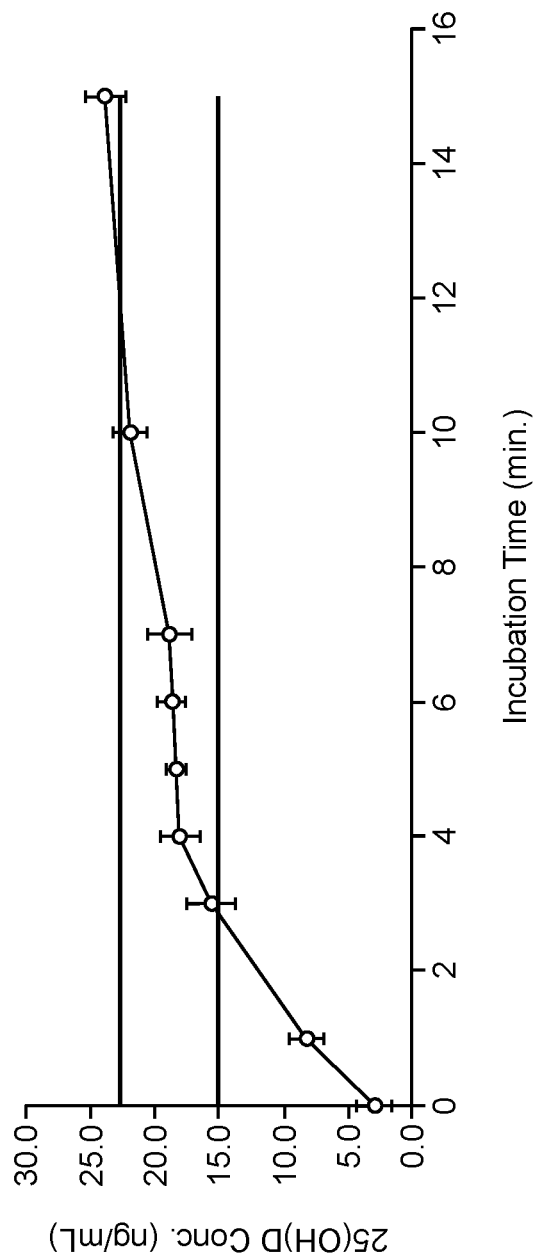
FIG. 7 is a graph showing the concentration of 25OH Vitamin D, in ng/mL, as a function of incubation time, in minutes, with a processing reagent.

Another study was conducted where blood samples were incubated for different periods of time with a processing reagent, as described in Example 8. A processing reagent of $IO_4$ and $MnCl_2$ in water was incubated at room temperature (23-25° C.) with blood samples for 0 minutes, 1 minute, 3 minutes, 4 minutes, 5 minutes, 10 minutes, 13 minutes, 14 minutes, 15 minutes, or 16 minutes. After the incubation period had elapsed, an aliquot of the extracted sample was pipetted onto a lateral flow immunoassay for detection of 25 OH Vitamin D Results are shown in FIG. 7. In FIG. 7, the concentration of 25OH Vitamin D, in ng/mL, as a function of extraction time, in minutes, is shown. The solid lines in the graph represent a ±20% accuracy limit for a QC standard. As seen, incubation times of between 3-12 minutes provided a more accurate result. Thus, in one embodiment, the sample and the processing reagent are incubated for a period ranging from 2-15 minutes, 3-12 minutes, 4-12 minutes, or 4-11 minutes.

Accordingly, in one embodiment, a method to detect presence of vitamin D or a metabolite of vitamin D in a blood sample is contemplated. The method comprises combining a blood sample with a solution comprising metaperiodate and manganese to form a mixture; and detecting vitamin D or a metabolite of vitamin D in the mixture. In the method, the sample can be combined with the solution at a ratio of between about 1:4 to 1:10 (sample:solution). The metaperiodate in the solution is generally in the form of a metaperiodate anion dissociated periodically from a sodium cation. In one embodiment, the solution comprises between about 0.2-0.4 M metaperiodate. In other embodiments, the solution comprises manganese, for example, a manganese salt that is added to the solution, and manganese sulfate, manganese chloride and manganese carbonate are exemplary. The manganese is present in the solution at a concentration of between about 0.5-0.9 mM, in some embodiments. A specific example of a solution is one comprising 0.3M sodium metaperiodate and 0.7 mM manganese chloride.

The solution is preferably an aqueous based solution, with water or a buffer as a main ingredient. In one embodiment, it is a buffer, such as a sodium acetate buffer. One specific example is a solution comprising 14 mM sodium acetate and its pH is adjusted to be between about pH 5-5.5.

The present disclosure encompasses the use of periodate to treat patient samples, thereby providing a method which is faster, more convenient, and which is not detrimentally affected by the presence of vitamin D binding protein (DBP). As illustrated by the examples, it was found that metaperiodate can be added to a subject's whole blood (or plasma or serum), resulting in a sample which can be directly applied to a lateral immunoassay strip. Vitamin D is tightly bound to DPB in circulation. To free vitamin D from the DPB, a variety of strong reagents have been tried to enable a rapid, simple and reliable extraction technique in plasma. The problem becomes significantly more difficult when trying to extract vitamin D in the presence of whole blood, and permit a processed sample that can be placed on an immunoassay test strip.

In one aspect, a sample, such as a whole blood sample, is mixed with a solution of metaperiodate and incubated at a temperature above room temperature prior to detecting and/or measuring vitamin D or a vitamin D metabolite in the sample. In a second aspect, the sample from a subject is mixed with a solution containing both metaperiodate and a metal salt, then incubated at room temperature for a brief period of time prior to detecting and/or measuring vitamin D or a vitamin D metabolite in the sample.

While the examples provided herein are directed to the detection of 25OHD, it is understood that the use of metaperiodate for sample processing prior to detection of vitamin D (including Vitamin $D_2$ and vitamin $D_3$) or any vitamin D metabolite (e.g., $24,25(OH)_2D$ or $25,26(OH)_2D$). The term "analyte" as used herein refers to the molecule being detected in an assay, such as 25OHD. It is understood that antibodies to an analyte may bind to analytes for both vitamin D2 and D3 (i.e., $25OHD_2$ and $25OHD_3$). In some embodiments, an antibody may be used which is specific for $25OHD_2$ or $25OHD_3$.

In a first aspect, to measure 25OHD in a sample, metaperiodate is added to a concentration approaching saturation at a dilution ranging from about 1:4 to 1:8. In a preferred embodiment, the sample is whole blood, however, the sample may be, e.g., serum or plasma. Serum or plasma is prepared from whole blood according to methods well known to the ordinarily skilled artisan. A concentrated solution of metaperiodate in water is used. In one embodiment, the solution contains 0.22M metaperiodate and 0.5 mM $MnCl_2$ with 10 mM sodium acetate pH 4.5. In some embodiments, the metaperiodate is a salt such as sodium metaperiodate. The metaperiodate used can have a concentration of about 0.1 M to 0.5 M, 0.2 M to 0.4 M, 0.2 M to 0.4 M, or about 0.22 M, 0.35 M, or 0.46 M. The metaperiodate solution is added to the subject sample at a ratio of metaperiodate:sample ranging from about 1:2 to 1:12, 1:4 to 1:8, 1:8 to 1:12, or 1:8 to 1:10. In some embodiments, the manganese is added as a solid to a final concentration of about 25 mM to 150 mM, 50 mM to 120 mM, or 75 mM to 105 mM manganese.

In an alternative aspect of the present disclosure, a whole blood sample is treated with metaperiodate in the presence of a metal salt. In one embodiment, the metal salt is manganese in an oxidation level +2 ($Mn^{2+}$) with a counter ion, such as chloride, however, other metal salts are contemplated such as manganese sulphate. It is shown herein that the addition of $Mn^{2+}$ acts as a catalyst which greatly accelerates the extraction process in which 25ODH is separated from DBP in a whole blood, serum or plasma samples. In the absence of $Mn^{2+}$, the dissociation proceeds to completion in more than 30 minutes at room temperature or within about 5-10 minutes at 40° C. However, by adding or $MnCl_2$ or $MnSO_4$ to the metaperiodate and then mixing with a sample at room temperature, the dissociation is complete in about 3 to 5 minutes. Accordingly, the present disclosure includes the use of a metal salt in combination with metaperiodate to generate a metaperiodate/salt solution which is mixed with a sample which may be whole blood, plasma or serum.

Accordingly, and in one embodiment, the present disclosure is directed to methods for extracting vitamin D or a vitamin D metabolite and/or to measuring vitamin D and its metabolites in a sample from a human or non-human subject. The method finds use in measuring or detecting vitamin D, including the metabolite 25-OH vitamin D (25OHD). Reference herein to 25OHD intends total 25-OH vitamin D which is a combined measurement of two major forms, vitamin D2 (ergocalciferol) and vitamin D3 (cholecalciferol), known collectively as calciferol. It is contemplated, however, that the methods disclosed herein can be applied to an assay which measures only ergocalciferol or only cholecalciferol.

In an exemplary embodiment, a lateral flow device is prepared for measuring levels of vitamin D extracted from whole blood, plasma or serum as described above. The lateral flow device comprises a membrane having a test line to which vitamin D conjugated to a carrier protein is bound. The assay is performed in part by incubating a sample with a monoclonal antibody which specifically binds to 25OHD2 and/or 25OHD3, wherein the monoclonal antibody is conjugated to a bead (e.g., a latex bead) having a fluorescent label. Accordingly, when a patient sample prepared as described herein is incubated with the monoclonal antibody then applied to a sample loading pad, the sample flows through the membranes of the device and passes through the test line, where only monoclonal antibodies having free binding sites are able to bind to the vitamin D attached to the membrane. The device is then analyzed using a reader to determine the amount of labeled monoclonal antibody bound to the test line.

In another embodiment, a sample mixture obtained through a metaperiodate treatment as described above is measured for the presence of 25OHD using a solid phase ELISA assay in which the wells of a microtiter plate are coated with an immunoglobulin specific for 25OHD. Aliquots of the sample mixture and various controls are placed into each of the wells and incubated over a time period sufficient to allow 25OHD to dissociate from DBP. Labeled 25OHD (e.g., labeled with biotin and mixed with horseradish peroxidase) is then added to individual wells to compete with unlabeled 25OHD present on the binding sites of the specific immunoglobulin. Eventually, reagents are added to produce a detectable and measurable reduction in the total signal in wells in which labeled 25OHD has bound to the immunoglobulin. As with the lateral flow assay, the solid phase ELISA assay is well known to the ordinarily skilled artisan (e.g., see the Technical Data Sheet for Quidel MicroVue™ Bone).

As discussed above, mixing a whole blood sample with metaperiodate surprisingly generates a mixture that is not too viscous for application to a lateral flow immunoassay strip or other such assay requiring flow of the mixture and components through a solid support. A lateral flow assay strip can be prepared by coating the antibody or a plurality of antibodies in an array on solid support. This strip can then be dipped into the test biological sample and then processed quickly through washes and detection steps to generate a measurable signal, such as for example a colored spot. The sample flows along a flow path running from the sample receiving zone (upstream), through the label zone (midstream), and then to the observation area (downstream). Optionally, the fluid may thereafter flow to the absorbent zone.

In one embodiment, the sample receiving zone is made of an absorbent application pad. Suitable materials for manufacturing absorbent application pads include, but are not limited to, hydrophilic polyethylene materials or pads, glass fiber filter paper or pads, desiccated paper, paper pulp, fabric, and the like. In a related embodiment, the sample receiving zone is constructed from any material that absorbs water. It is understood that any vitamin D or vitamin D metabolite in the sample applied to the sample receiving zone can flow through the lateral strip and bind to antibody embedded in and/or immobilized on the strip. Such lateral flow devices are well known in the art. Full descriptions can be found, for example, in U.S. Pat. Nos. 5,075,078, 7,537, 937, and 8,617,486.

In one embodiment of a lateral flow immunoassay device, a sample mixture prepared as described above is applied at a sample loading pad and then flows through the conjugate pad to the test membrane. In one embodiment, the sample loading pad comprises a glass fiber membrane which binds to, for example, red blood cells in the sample, allowing the vitamin D-containing (soluble) portion of the sample to readily flow through the lateral flow device membranes. Alternatively or additionally, the sample mixture, prior to applying to the loading pad, may be centrifuged to remove some, most or all of the red blood cells to facilitate flow of the sample through the assay strip. In another embodiment, prepared sample may be treated in a way to reduce the pH of the sample, precipitating out extra protein and blood cells which are subsequently removed by centrifugation. In one embodiment, the sample is prepared in a bottle which is fitted with a filter cap, e.g., a dropper bottle with a filter in the tip, such that the sample is filtered as it is applied to the loading pad.

According to the present disclosure, it is envisioned that antibodies conjugated to a physically detectable label (to form a labeled detection antibody) are in solution and as the sample passes through the conjugate pad, complexes are formed between the antibodies and the analyte (vitamin D or vitamin D metabolite(s)). In one embodiment, the lateral flow assay is an inhibition assay wherein vitamin D or vitamin D metabolite is conjugated to the membrane (e.g., through a carrier protein) and the quantity of labeled detection antibody which is able to bind to the vitamin D or vitamin D metabolite conjugated to the test site decreases as the quantity of vitamin D or vitamin D metabolite in the sample increases. The test strip is then inserted into a reader, where the signal from the label in the complex is measured. As the amount of vitamin D or vitamin D metabolite in the samples increases, the signal emitted from the test strips decreases accordingly.

The test strip may be enclosed within a housing that includes an identifying symbol, such as a bar code, which is also read by the reader and contains data related to the assay device and/or test run. The greater the amount of Vit D that has bound to the detection antibody bound to the detection beads the greater the reduction in the total signal on the analyte test line. In one embodiment, the device can further comprise a control site (C) at which analytes that recognize the labeled antibody in the conjugate pad is immobilized.

III. Kits

In another aspect, a kit for processing a sample for detection of an analyte of interest free of its binding protein in vivo is provided. The kit comprises one of (i) a container comprising a solution comprising sodium metaperiodate and manganese chloride; or (ii) a first container comprising a solution comprising sodium metaperiodate and a second container comprising manganese chloride; and instructions for use.

In one embodiment, the solution comprising sodium metaperiodate is an aqueous buffer of sodium acetate. In another embodiment, the solution comprising sodium metaperiodate has a concentration of sodium metaperiodate of between about 0.1-0.5M.

In another embodiment, the solution comprising manganese chloride has a concentration of manganese chloride of between about 0.1-1 mM.

The instructions for use, in one embodiment, instruct mixing the solution comprising sodium metaperiodate with a sample, such as a sample in which vitamin D or a metabolite of vitamin D is desired to be detected, a sample to solution ratio of between about 1:2 to 1:15.

The kit may further comprise an immunoassay. In embodiments where the kit is for use in detecting vitamin D or a metabolite thereof, the immunoassay comprises an antibody which binds a vitamin D metabolite.

Also contemplated herein are kits for the extraction of vitamin D or metabolite thereof. In one aspect, the kit contains metaperiodate. In another embodiment, the metaperiodate is present in the kit as a solution or in a solid form. If the metaperiodate in the kit is a solution, the solution can have a concentration of about 0.2 M to 0.7 M, 0.3 M to 0.6 M, or 0.4 M to 0.5 M. In one embodiment, the metaperiodate solution has a concentration of about 0.22 M. The kit may contain a sample collection container and instructions for use.

In another embodiment, a kit is provided which contains metaperiodate as a solid or a solution. The solution can have a concentration of about 0.2 M to 0.7 M, 0.3 M to 0.6 M, or 0.4 M to 0.5 M. The kit may further comprise a solution of a metal salt, such as manganese chloride. The manganese chloride may be provided in water at a concentration from about 0.1 mM to 1 mM or about 0.5 mM. In an alternative embodiment, the metaperiodate and manganese salt are provided in a single liquid medium, wherein the metaperiodate and manganese salt are each present in the solution in the same concentrations as described above. The kit may further comprise a container of a divalent metal ion chelator such as EDTA. The kit may further contain a sample collection container and instructions for use. In one embodiment, the sample collection container is a minivette POCT dispensing device.

In one embodiment, the kit further comprises a lateral flow immunoassay device as described above, wherein the device contains reagents for detection of vitamin D or a metabolite of vitamin D.

IV. Examples

The following examples are illustrative in nature and are in no way intended to be limiting.

EXAMPLE 1

Sample Preparation Using a Processing Reagent Comprising Metaperiodate

A processing reagent was prepared by dissolving sodium metaperiodate ($NaIO_4$) in water (0.23 M $IO_4$).

Samples were prepared by spiking a known amount (20 ng/mL, 60 ng/mL and 100 ng/mL) of 25OHD3 (vitamin D metabolite) QC standard into a fixed volume of albumin diluent and of human serum. The samples were processed with the processing reagent or, as negative control, a processing reagent lacking the metaperiodate (0M $IO_4$) by combining the sample and the processing reagent and incubating for 40 minutes at room temperature.

After incubation, aliquots from the samples were tested in replicates of ten (n=10), each aliquot placed on an immunoassay test device with an antibody for the vitamin D metabolite attached to fluorescent label. Signal from the fluorescent label present in a test zone of the immunoassay device, which correlates with the amount of vitamin D metabolite in the test zone, was measured using a commercially-available instrument with an optical system for detection of fluorescent signal (Sofia® Analyzer, from Quidel Corporation). Results are presented in Tables 1A-1B and in FIGS. 1A-1B, wherein a decrease in signal (RFU) indicates an increase in analyte detection.

TABLE 1A

Treatment of albumin sample and analysis for Vitamin D Metabolite

| Periodate Concentration in Processing Reagent | Conc. of 25OH D3 in Albumin Solution (ng/mL) | Signal from Label attached to antibody for 25OD D3 (RFU) | % CV | Signal/ Background Ratio from Optical Analyzer (S/B) |
|---|---|---|---|---|
| 0M $IO_4$ | 0 | 260036 | 6.2% | 1.00 |
|  | 20 | 199632 | 13.6% | 0.77 |
|  | 60 | 127424 | 31.3% | 0.49 |
|  | 100 | 84495 | 40.2% | 0.32 |
| 0.23M $IO_4$ | 0 | 215738 | 9.9% | 1.00 |
|  | 20 | 63994 | 18.0% | 0.30 |
|  | 60 | 16801 | 15.2% | 0.08 |
|  | 100 | 11838 | 15.1% | 0.05 |

TABLE 2A

Treatment of human serum sample and analysis for Vitamin D Metabolite

| Periodate Concentration in Processing Reagent | Conc. of 25OH D3 in human serum sample (ng/mL) | Signal from Label attached to antibody for 25OD D3 (RFU) | % CV | Signal/ Background Ratio from Analyzer (S/B) |
|---|---|---|---|---|
| 0M IO$_4$ | 0 | 198030 | 11.5% | 1.00 |
|  | 20 | 209960 | 20.3% | 1.06 |
|  | 60 | 205327 | 15.6% | 1.04 |
|  | 100 | 198266 | 15.3% | 1.00 |
| 0.23M IO$_4$ | 0 | 142114 | 11.7% | 1.00 |
|  | 20 | 79737 | 23.8% | 0.56 |
|  | 60 | 28965 | 26.9% | 0.20 |
|  | 100 | 20152 | 26.1% | 0.14 |

EXAMPLE 2

Processing Reagent with Heat as a Catalyst

Samples with vitamin D3 metabolite spiked at known concentrations (6.1 ng/mL, 17.6 ng/mL, 33.4 ng/mL and 97.4 ng/mL) into human serum were prepared.

A processing reagent was prepared by dissolving sodium metaperiodate (NaIO$_4$) in water (0.23 M IO$_4$).

The samples were processed by combining sample and processing reagent at a 1:8 ratio to form a mixture. The mixture was heated to a test temperature (25° C., 37° C., 40° C., 55° C., 65° C., 75° C. and 85° C.) for a time period of 4 minutes, 6 minutes, 8 minutes, 12 minutes or 14 minutes. The concentration of vitamin D3 metabolite in the processed samples was measured using an optical reader. Results for the samples processed using a 55° C. temperature (as representative of the data) are shown in Table 2 and in FIGS. 2A-2B.

EXAMPLE 3

Processing Reagents with Various Metaperiodate Concentrations

Processing reagents were prepared by dissolving sodium metaperiodate (NaIO$_4$) in water to provide processing reagents with metaperiodate concentrations ranging from 0.1M to 0.6M IO$_4$.

Samples were prepared from human serum and vitamin D3 metabolite. The samples and processing reagents were combined in dilution ratios of sample to extraction reagent ranging from 1:1 (equal parts of each) to 1:15 (1 volume of sample to 15 volumes of processing reagent), and incubated at 55° C. for 10 minutes. Concentration of vitamin D3 metabolite in the processed samples was measured using a competitive inhibition immunoassay test strip for vitamin D and a commercially available instrument (Sofia® Analyzer, from Quidel Corporation). Lower dilutions such as 1:1 and 1:3 in some cases gave matrix effects with some patient samples which were not observed with higher dilutions. To assess accuracy of the measurements, the human serum samples without processing by the processing reagent were analyzed for vitamin D metabolite concentration by LC-MS/MS. The correlation between the measurements in shown in FIG. 3, where vitamin D metabolite concentrations measured in samples processed with a processing reagent of 0.318 M IO$_4$ using a 1:7 dilution, with an extraction time of 10 minutes at 55° C., are compared with the concentration measured by LC-MS/MS.

EXAMPLE 4

Processing of Various Sample Types: Whole Blood, Serum and Plasma

Extraction of vitamin D using an extraction reagent with metaperiodate and heat, at a temperature of 55° C., was

TABLE 2

| Condition | Time [min] | Sample ID | Conc. [ng/mL] | Signal [RFU] | STDEV | % CV | S/B | ST-DEV | % CV |
|---|---|---|---|---|---|---|---|---|---|
| 1 | 4 | Depleted Serum | 0 | 152,766 | 15,497 | 10.1% | 1.00 | 0.10 | 10.1% |
| 2 |  | Unit #32 | 6.1 | 122,151 | 13,379 | 11.0% | 0.80 | 0.09 | 11.0% |
| 3 |  | Patient #1 | 17.6 | 96,475 | 12,624 | 13.1% | 0.63 | 0.08 | 13.1% |
| 4 |  | Patient #30 | 33.4 | 86,245 | 12,807 | 14.8% | 0.56 | 0.08 | 14.8% |
| 5 |  | Patient #38 | 97.4 | 31,340 | 5,504 | 17.6% | 0.21 | 0.04 | 17.6% |
| 6 | 6 | Depleted Serum | 0 | 149,597 | 12,563 | 8.4% | 1.00 | 0.08 | 8.4% |
| 7 |  | Unit #32 | 6.1 | 120,762 | 17,440 | 14.4% | 0.81 | 0.12 | 14.4% |
| 8 |  | Patient #1 | 17.6 | 83,046 | 11,877 | 14.3% | 0.56 | 0.08 | 14.3% |
| 9 |  | Patient #30 | 33.4 | 66,711 | 7,288 | 10.9% | 0.45 | 0.05 | 10.9% |
| 10 |  | Patient #38 | 97.4 | 22,771 | 4,190 | 18.4% | 0.15 | 0.03 | 18.4% |
| 11 | 8 | Depleted Serum | 0 | 156,619 | 19,005 | 12.1% | 1.00 | 0.12 | 12.1% |
| 12 |  | Unit #32 | 6.1 | 105,214 | 14,255 | 13.5% | 0.67 | 0.09 | 13.5% |
| 13 |  | Patient #1 | 17.6 | 76,062 | 13,597 | 17.9% | 0.49 | 0.09 | 17.9% |
| 14 |  | Patient #30 | 33.4 | 61,259 | 6,924 | 11.3% | 0.39 | 0.04 | 11.3% |
| 15 |  | Patient #38 | 97.4 | 19,289 | 2,794 | 14.5% | 0.12 | 0.02 | 14.5% |
| 16 | 12 | Depleted Serum | 0 | 149,480 | 22,450 | 15.0% | 1.00 | 0.15 | 15.0% |
| 17 |  | Unit #32 | 6.1 | 108,804 | 13,431 | 12.4% | 0.72 | 0.09 | 12.4% |
| 18 |  | Patient #1 | 17.6 | 82,616 | 11,135 | 13.5% | 0.55 | 0.07 | 13.5% |
| 19 |  | Patient #30 | 33.4 | 61,628 | 12,833 | 20.8% | 0.41 | 0.09 | 20.8% |
| 20 |  | Patient #38 | 97.4 | 20,682 | 4,716 | 22.8% | 0.14 | 0.03 | 22.8% |
| 21 | 14 | Depleted Serum | 0 | 150,198 | 11,910 | 7.9% | 1.00 | 0.08 | 7.9% |
| 22 |  | Unit #32 | 6.1 | 104,347 | 10,993 | 10.5% | 0.69 | 0.07 | 10.5% |
| 23 |  | Patient #1 | 17.6 | 78,729 | 10,375 | 13.2% | 0.52 | 0.07 | 13.2% |
| 24 |  | Patient #30 | 33.4 | 57,953 | 8,134 | 14.0% | 0.39 | 0.05 | 14.0% |
| 25 |  | Patient #38 | 97.4 | 18,868 | 2,816 | 14.9% | 0.13 | 0.02 | 14.9% | performed on whole blood, serum and plasma samples obtained from a single subject in order to evaluate the consistency of the procedure using the different sample types. A blood sample was taken from 10 subjects, and each of the 10 samples separated into individual samples of serum, plasma and whole blood for a total of 30 samples from 10 patients. Vitamin D3 metabolite was added. Each sample was processed using an extraction reagent comprising 0.318 M $IO_4$ in water and heat at 55° C. for 10 minutes. Vitamin D concentration in each processed sample was determined using a competitive inhibition immunoassay test strip for vitamin D and a commercially available instrument (Sofia® Analyzer, from Quidel Corporation). In addition, vitamin D concentration in unprocessed samples of whole blood (samples not treated with the extraction reagent) was measured by LC-MS/MS. Results are shown in FIGS. 4A-4B.

EXAMPLE 5

Processing Reagents with a Chemical Catalyst

A processing reagent comprising metaperiodate (0.318M $IO_4$) and manganese sulfate ($MnSO_4$; 0.5 mM manganese) in water was prepared.

A pooled serum sample with vitamin D metabolite was prepared. The sample and the processing reagent were contacted at a ratio of 1 part sample to 8 parts processing reagent. Aliquots were taken over a 30 minute room temperature incubation period and assayed for vitamin D metabolite concentration. Extent of vitamin D metabolite extraction as a function of time is shown in FIG. 5.

EXAMPLE 6

Processing Reagents with a Chemical Catalyst

Processing reagents comprising metaperiodate at concentrations ranging from 0.195M to 0.4M and manganese chloride ($MnCl_2$) at manganese concentrations ranging from 0.1 mM to 0.6 mM in water were prepared.

A blood sample was taken from 10 subjects, and each of the 10 samples separated into individual samples of serum, plasma and whole blood for a total of 30 samples from 10 patients. Vitamin D3 metabolite was added.

Each sample was processed using the processing reagents, and vitamin D concentration in each processed sample was determined using a competitive inhibition immunoassay test strip for vitamin D and a commercially available instrument (Sofia® Analyzer, from Quidel Corporation). In addition, vitamin D concentration in unprocessed samples of whole blood, serum and plasma (samples not treated with the extraction reagent) was measured by LC-MS/MS.

Data for the samples processed with an extraction reagent comprised of 0.22M metaperiodate, 0.5 mM manganese (as manganese chloride) and a sample:extraction reagent ratio of 1:10 are shown in FIGS. 6A-6B.

EXAMPLE 7

Effects of the Extraction Procedure on Whole Blood

The effects of the metaperiodate extraction on a whole blood sample were visualized. Whole blood samples were treated as described in Example 6: incubation with 0.22M $IO_4$ and 0.5 mM $MnCl_2$ at a sample:extraction reagent dilution factor of 1:10. Upon addition of whole blood to the magenta colored extraction reagent, the reaction appeared bright red in color. During the 5 minute room temperature incubation, the color changed to a dark brown color. This color appeared to come from the red blood cells themselves. When the extracted sample was applied to the glass fiber pad of a lateral flow device, the red blood cell portion appeared to remain in the matrix of the glass fiber pad, allowing only the extracted plasma to move into the nitrocellulose membrane (data not shown).

EXAMPLE 8

Detection of 25OH Vitamin D in Blood

A study was conducted to evaluate the effect of incubation time of sample with the extraction reagent on detection of 25OH Vitamin D from blood samples. 100 µL of patient blood samples were added to 600 µL of extraction reagent (0.22M $IO_4$ and 0.5 mM $MnCl_2$), the tube with the sample and the extraction reagent was inverted two times and then incubated at room temperature (23-25° C.) for 0 minutes, 1 minute, 3 minutes, 4 minutes, 5 minutes, 10 minutes, 13 minutes, 14 minutes, 15 minutes, or 16 minutes. After the incubation period had elapsed, 120 µL of the extracted sample was pipetted onto a lateral flow immunoassay for detection of 25 OH Vitamin D and a commercially available instrument (Sofia® Analyzer, from Quidel Corporation). Results are shown in FIG. 7.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method to process and assay a sample, comprising:
   providing a sample suspected of comprising vitamin D or a metabolite of vitamin D each bound to a binding protein;
   contacting the sample with a processing reagent comprising between about 0.2 M to about 0.45 M metaperiodate at a ratio of between about 1:2 and 1:12 to form a mixture;
   exposing the mixture to a catalyst that is heat or a manganese salt; and
   assaying the mixture by performing an immunoassay comprising contacting an aliquot of the mixture with an antibody that specifically binds vitamin D or vitamin D metabolite to detect vitamin D or vitamin D metabolite in the sample, wherein exposing the mixture to a catalyst that is heat comprises incubating the mixture at a temperature above 25° C. and less than 90° C.

2. The method of claim 1, wherein the contacting and the exposing occur sequentially.

3. The method of claim 1, wherein the contacting and the exposing occur essentially simultaneously.

4. The method of claim 1, wherein the sample is exposed to the manganese salt in the contacting step by contacting the sample with a processing reagent comprising metaperiodate and the manganese salt.

5. The method of claim 1, wherein the mixture is contacted with a solution comprising the manganese salt.

6. The method of claim 1, wherein the catalyst is a manganese salt.

7. The method of claim 6, wherein the manganese salt is manganese chloride.

8. The method of claim 1, wherein contacting comprises contacting the sample with a processing reagent comprising the metaperiodate in the form of a metaperiodate anion intermittently associated with a cation of sodium.

9. A method to detect presence of vitamin D or a metabolite of vitamin D in a blood sample, comprising:
   combining a blood sample with a solution comprising between about 0.2 M to about 0.45 M metaperiodate and manganese salt to form a mixture;
   detecting vitamin D or a metabolite of vitamin D in the mixture by performing an immunoassay comprising contacting an aliquot of the mixture with an antibody that specifically binds vitamin D or vitamin D metabolite, wherein the ratio of the blood sample to the solution is between about 1:4 and 1:10.

* * * * *